(12) United States Patent
Pujol Ramo et al.

(10) Patent No.: US 8,764,191 B2
(45) Date of Patent: Jul. 1, 2014

(54) SYSTEM AND METHOD FOR CHARACTERIZING THE OPTICAL QUALITY AND THE PSEUDO-ACCOMMODATION RANGE OF MULTIFOCAL MEANS USED FOR CORRECTING VISUAL DEFECTS

(75) Inventors: Jaume Pujol Ramo, Barcelona (ES); Sergio Òscar Luque, Barcelona (ES); Fernando Díaz Doutón, Terrassa (ES)

(73) Assignee: Universitat Politècnica de Catalunya (ES)

( * ) Notice: Subject to any disclaimer, the term of this patent is extended or adjusted under 35 U.S.C. 154(b) by 29 days.

(21) Appl. No.: 13/696,083

(22) PCT Filed: May 3, 2011

(86) PCT No.: PCT/ES2011/070316
§ 371 (c)(1),
(2), (4) Date: Jan. 16, 2013

(87) PCT Pub. No.: WO2011/138487
PCT Pub. Date: Nov. 10, 2011

(65) Prior Publication Data
US 2013/0188131 A1  Jul. 25, 2013

(30) Foreign Application Priority Data
May 4, 2010  (ES) .................................. 201000593

(51) Int. Cl.
*A61B 3/14*  (2006.01)
*A61B 3/10*  (2006.01)

(52) U.S. Cl.
USPC ........................................................ 351/206

(58) Field of Classification Search
USPC .................................................. 351/200–246
See application file for complete search history.

(56) References Cited

U.S. PATENT DOCUMENTS

| 6,623,117 B2 * | 9/2003 | Shibutani et al. ............. 351/211 |
| 7,001,020 B2 | 2/2006 | Yancey et al. |
| 7,481,535 B2 | 1/2009 | Yancey et al. |

(Continued)

FOREIGN PATENT DOCUMENTS

| ES | 2163373 AB | 1/2002 |
| ES | 2327704 AB | 11/2009 |

OTHER PUBLICATIONS

DataBase Biosis, No. PREV200510301734, Guell J.L. et al. "Accommodative IOLs objective evaluation using a novel double-pass based instrument", abstract, Aug. 8, 2011.

*Primary Examiner* — Mohammed Hasan
(74) *Attorney, Agent, or Firm* — Hess Patent Law Firm LLC; Robert J. Hess

(57) ABSTRACT

It is applied to bifocal, multifocal or progressive intraocular lenses or contact lenses, multifocal corneal ablation or other multifocal configurations, comprising means for projecting the image of a point light source on the retina of a patient and an assembly for directly recording the light reflected in said retina after the double passage of the light through the ocular means, integrating a first focus corrector device inserted in the path of the light beam guided towards the retina and a second focus correction device inserted in the light beam reflected from the retina, to be guided towards the mentioned recording means, each of said focus correction devices having independent control means for controlling the operation thereof.

10 Claims, 2 Drawing Sheets

(56) References Cited

U.S. PATENT DOCUMENTS

| | | |
|---|---|---|
| 2002/0063851 A1 | 5/2002 | Shibutani et al. |
| 2003/0025877 A1 | 2/2003 | Yancey |
| 2005/0110951 A1 | 5/2005 | Yancey et al. |
| 2011/0109877 A1 | 5/2011 | Pujol Ramo et al. |

* cited by examiner

SYSTEM AND METHOD FOR CHARACTERIZING THE OPTICAL QUALITY AND THE PSEUDO-ACCOMMODATION RANGE OF MULTIFOCAL MEANS USED FOR CORRECTING VISUAL DEFECTS

FIELD OF THE INVENTION

The invention described herein is encompassed within the field of visual optics, ophthalmology and optometry and is suitable for characterizing the optical quality and the pseudo-accommodation range of multifocal means including in said term bifocal, multifocal or progressive intraocular lenses or contact lenses, multifocal corneal ablation or other multifocal configurations, using a modification in the so-called double-pass technique based on projecting the image of a point object on the retina of a patient and directly recording the light reflected thereon, after the double passage of the light through the ocular means.

The present invention generally relates to a system and a method for evaluating/characterizing the optical quality and the pseudo-accommodation range of multifocal means suitable to be implemented both in vivo and in vitro.

BACKGROUND OF THE INVENTION

"Determination of the point-spread function of human eyes using a hybrid optical-digital method", J. Opt. Soc. Am. A, 4, 1109-1114 (1987) by J. Santamaría, P. Artal, J. Bescós describes the mentioned double-pass technique based on projecting a point light beam on the retina of the patient and directly recording the light reflected from it following the double passage of the light through the ocular means which allows obtaining the objective measurement of aberration and scattering contributions to ocular optical quality (F. Díaz-Doutón, A. Benito, J. Pujol, M. Arjona, J. L. Güell, P. Artal, "Comparison of the retinal image quality obtained with a Hartmann-Shack sensor and a double-pass instrument", Inv. Ophthal. Vis. Sci., 47, 1710-1716 (2006)).

The in vitro evaluation of the optical quality of multifocal intraocular lenses or contact lenses can be carried out using single-pass systems consisting of forming the image of an object on a CCD camera before the passage of the light through the multifocal means (Artigas J. M, Menezo J. L, Penis C, Felipe A., Diaz-Llopis M., "Image quality with multifocal intraocular lenses and the effect of pupil size", J Cataract Refract Surg 2007; 33:2111-2117 2007, Pieh S., Fiala W, Malz A, Stork W., "In Vitro Strehl Ratios with Spherical, Aberration-Free, Average, and Customized Spherical Aberration-Correcting Intraocular lenses" Invest. Ophthalmol. Vis. Science 50 1264-1270 (2009), Maxwell W. A., Lane S. S., Zhou F., "Performance of presbyopia-correcting intraocular lenses in distance optical bench tests" J Cataract Refract Surg 2009; 35:166-171). To take these measurements it is necessary to use an artificial eye where the multifocal system can be placed. The ISO 11979-2 [ISO 00] standard is available today providing the guidelines on how this eye should be and what conditions must be met to enable taking the measurement.

Double-pass technique with a conventional design in which the focus corrector is the same in the first and second passage has been used for evaluating the optical quality in multifocal intraocular lenses and contact lenses (Pujol, J.; Gispets, J.; Arjona, M. "Optical performance in eyes wearing two multifocal contact lens designs". Ophthalmic Physiol Opt., 2003, vol. 23, no. 4, p. 347-60, Gispets, J.; Arjona, M.; Pujol, J. "Image quality in wearers of a centre distance concentric design bifocal contact lens". Ophthalmic Physiol Opt., 2002, vol. 22, no. 3, p. 221-33, P. Artal, S. Marcos, R. Navarro, I. Miranda, and M. Ferro, "Through focus image quality of eyes implanted with monofocal and multifocal intraocular lenses" Opt. Eng. 34, 772-779 (1995), Fernández-Vega L, Madrid-Costa D., Alfonso J. F., Montés-Micó R., Poo-López A., "Optical and visual performance of diffractive infraocular lens implantation after myopic laser in situ keratomileusis" J Cataract Refract Surg 2009; 35:825-832, Castillo-Gómez A, Carmona-González D., Martinez-de-la-Casa J. M., Palomino-Bautista C, Garcia-Feijoo J., "Evaluation of image quality after implantation of 2 diffractive multifocal intraocular lens models" J Cataract Refract Surg 2009; 35:1244-1250). This technique can be used for taking measurements in vivo and in vitro, nevertheless it has a very significant limitation. In the first passage, upon forming the image of a point object on the retina, it will only be focused on a position of the focus corrector (generally the one corresponding to far vision), and upon introducing any other defocus for evaluating other vision conditions (near vision for example) this image will be defocused on the retina of the patient and therefore the image recorded on the camera in the second passage will be affected by the defocus occurring in the first passage.

The measurement of the ocular aberrations has also been used for characterizing the optical quality of multifocal intraocular lenses or contact lenses (Jeong, T. M.; Menon, M.; Yoon, G. "Measurement of wave-front aberration in the soft contact lenses by use of a Shack-Hartmann wave-front sensor". Applied Optics, 2005, vol. 44, no. 21, p. 4423-7, Martin, J. A.; Roorda, A. "Predicting and assessing visual performance with multizone bifocal contact lenses", Optom. Vis. Sci., 2003, vol. 80, no. 12, p. 812-19, Peyre, C.; Fumery, L.; Gatinel, D. "Comparison of high-order optical aberrations induced by different multifocal contact lens geometries". J Fr Ophtalmol., 2005, vol. 28, no. 6, p. 599-604). This technique also has significant limitations. On one hand, depending on the configuration of the sensor used for measuring ocular aberrations, it may have the same limitation as the conventional double-pass technique due to the defocus of the image of a point object on the retina formed in the first passage of the light through the eye. Another limitation of all these sensors is due to the difficulty in measuring the aberrations in discontinuous optical areas such as those found in multifocal intraocular lenses or contact lenses, particularly those having a refractive design. In fact, this difficulty or impossibility have been shown clearly in different published works (Charman W. N, Montés-Micó R., Radhakrishnan H., "Problems in the Measurement of Wavefront Aberration for Eyes Implanted With Diffractive Bifocal and Multifocal Intraocular lenses", Journal of Refractive Surgery Volume 24 March 2008, Jendritza B. B., Knorz M. C, Morton S., "Wavefront-guided Excimer Laser Vision Correction After Multifocal IOL Implantation", Journal of Refractive Surgery Volume 24 March 2008).

By analyzing the quality of images obtained for different defocuses, it is possible to determine the range in which the patient can see the images sharply enough, corresponding to the pseudo-accommodation range. Application WO2009133224 belonging to two of the present inventors describes a method and a system for the objective measurement of ocular accommodation wherein the mentioned double-pass technique is also used for its implementation.

BRIEF DESCRIPTION OF THE INVENTION

The invention is intended for providing a system for characterizing the optical quality and the pseudo-accommodation range of multifocal means used for correcting visual defects through retinal image analysis wherein devices for projecting the image of a point object on the retina of a patient and devices for directly recording the light reflected in said retina after the double passage of the light through the ocular means, are used, comprising at least one focus corrector device which is traversed by the light beam in its access path to the retina (illumination path) and by the light beam reflected from the retina (recording path).

According to the proposal of the invention, there is provided a system with a first focus correction device inserted in the path of the light beam guided towards the retina and a second focus correction device inserted in the light beam reflected from the retina, to be guided towards the mentioned recording means, each of said focus correction devices having independent control means for controlling the operation thereof, such that it allows focusing the image of a point light source in a differentiated manner on the retina of the patient through any of the foci of the intraocular lens and recording the double-pass image for different defocuses, including far and near vision, obtained with the second focusing system. According to an embodiment of the invention, said focus correction devices are formed by respective motorized optometers forming part of a double-pass ophthalmoscopic device which includes two lenses and two mirrors with an adjustable relative distance between them. However, this same optometer may have other configurations such as only two lenses with a variable distance between them, for example.

In an alternative embodiment it has been envisaged that at least one of said focus correction devices of the proposed system is made up of a lens with variable power.

The system has means which will be indicated in the following detailed description for displaying a fixation stimulus to the patient which overlaps the light beam striking the retina.

Likewise, the system of the invention will include means for viewing a patient's eye by means of an illumination system and a system for forming the image of the eye in a recording means such as a camera.

In order to be able to adjust the system to different pupil diameter values, the entrance and exit pupils of the optical system have a variable diameter. Both pupils are conjugated with the pupil of the patient's eye.

Other features of the invention as well as the details concerning the method will become clear in light of the following detailed description provided by way of non-limiting example.

DETAILED DESCRIPTION OF AN EMBODIMENT

Figure 1:
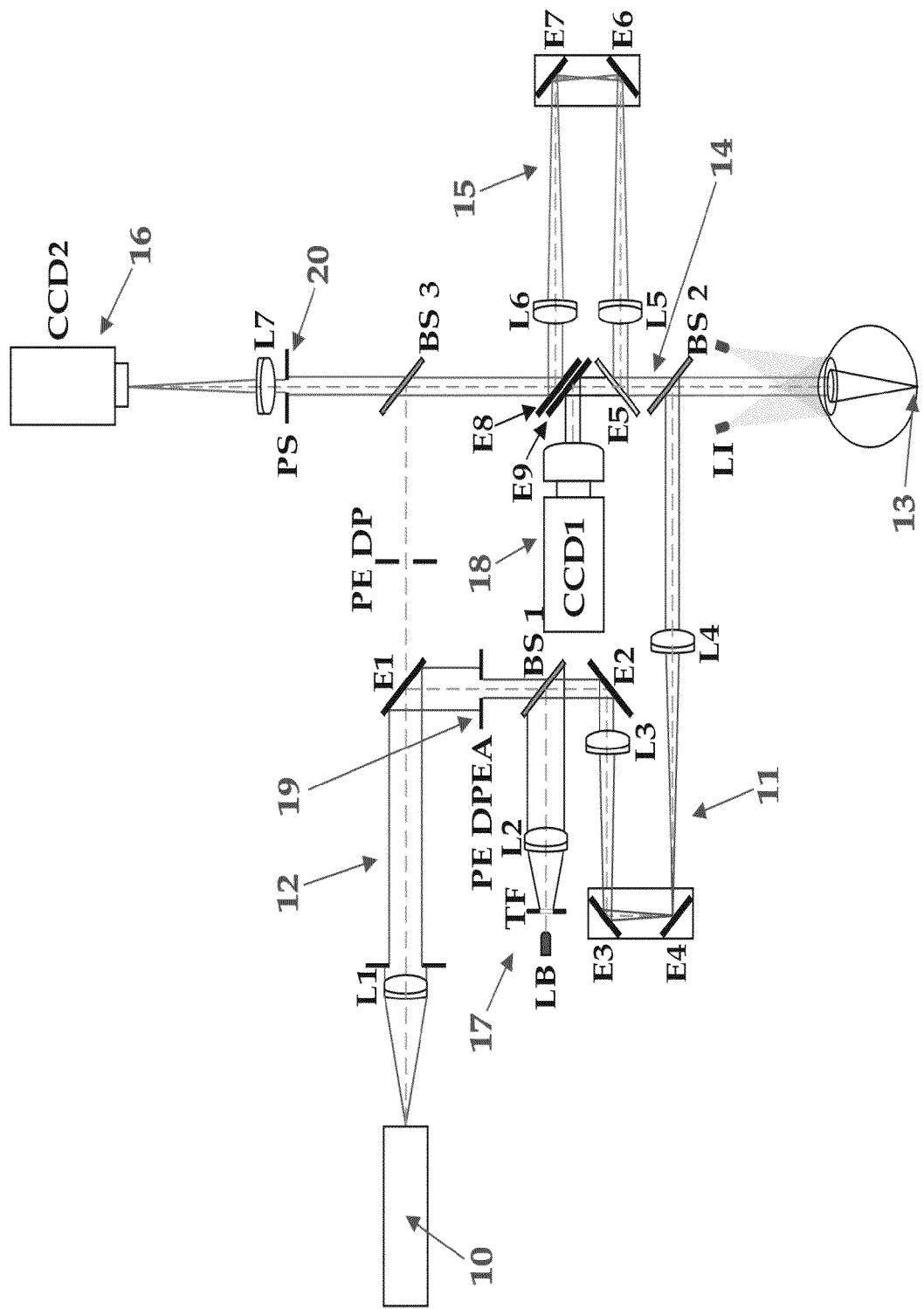
FIG. 1 shows a diagram of a possible construction of a system according to the proposal of this invention, wherein the focus correction devices have been implemented in the form of a motorized optometer having a pair of mirrors and lenses.

The diagram of FIG. 1 shows means for projecting the image of a point light source on the retina of a patient and means for directly recording the light reflected in said retina after the double passage of the light through the ocular means according to the principles of the present invention.

A point light source 10 and a first focus correction device 11 formed by a motorized optometer including two lenses L3, L4 and two mirrors E3, E4 with an adjustable relative distance between them, inserted in the path of the collimated light beam 12 guided towards retina 13, and a second focus correction device 15 made up of a motorized optometer including two lenses L5, L6 and two mirrors E6, E7 with an adjustable relative distance between them inserted in the light beam 14 reflected from the retina 13 to be guided towards a camera 16 or other recording means can thus be seen. According to the proposal of this invention, each of said focus correction devices 11, 15 has independent control means for controlling the operation thereof, such that it allows focusing the point light source 10 on the retina 13 of the patient through any of the focal points of the intraocular lens and introducing any defocus in the recording path at the same time.

Alternatively, and even though it has not been depicted, it is indicated that said focus correction devices only comprise two lenses with a variable distance between them or a lens with a variable power.

The drawing also shows that means 17 have been provided for displaying a fixation stimulus to the patient which overlaps the beam 12 focused on the retina 13.

Likewise, means 18 for viewing a patient's eye by means of an illumination system (L1) and a device for forming the image of the eye in a recording means (CCD1) are integrated in the system.

The system integrates entrance pupil 19 and exit pupil 20 of the optical system with a variable diameter. Both pupils are conjugated with the pupil of the patient's eye The method according to the invention consists of a method for characterizing the optical quality and the pseudo-accommodation range of multifocal means based on retinal image analysis by projecting the image of a point light source on the retina of a patient and directly recording the light reflected in said retina after the double passage of the light through the ocular means, characterized by applying at least one focus correcting step both in the illumination path and in the recording path.

Figure 2:
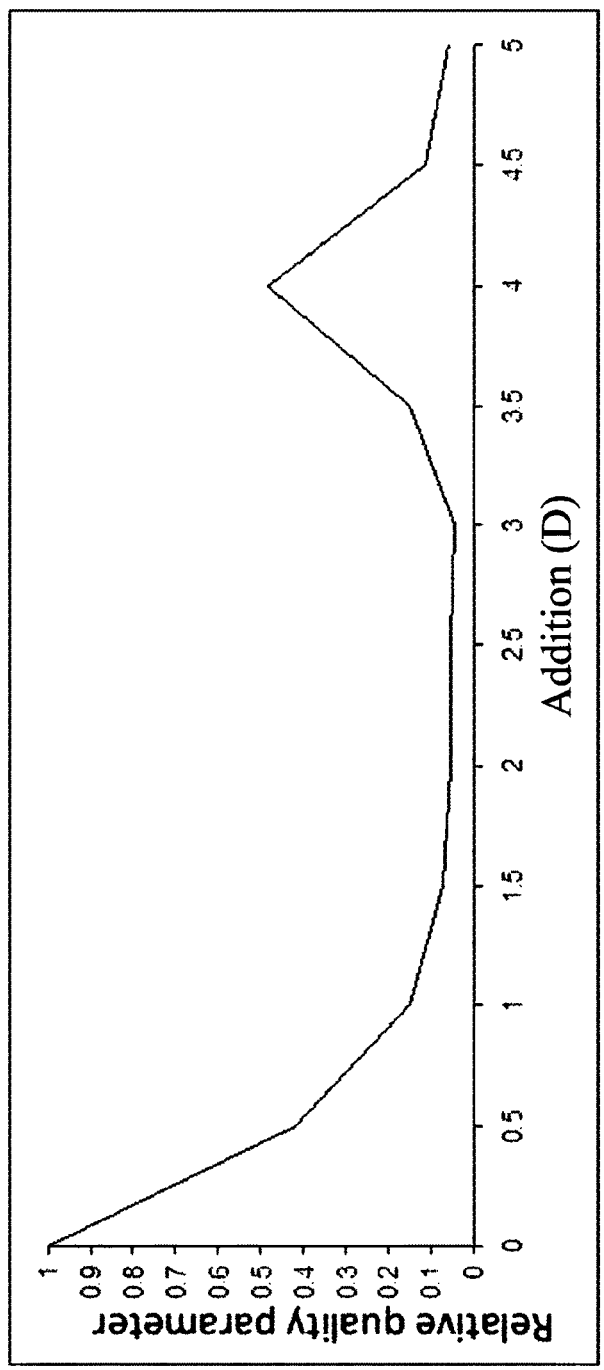
FIG. 2 shows an example of a defocus curve, the diopters applied are shown in the x-axis and the relative quality parameter for each case is shown in the y-axis.

The invention proposes two independent focus correcting steps, the first step occurs in the light beam of the illumination path and the second step occurs in the reflected light beam which must be recorded, providing an asymmetrical focus and the examination of the two near vision and far vision foci, and any focus corresponding to intermediate vision. By analyzing the quality of the retinal image obtained for the different foci, it is possible to obtain the defocus curve of the multifocal means, depicting an optical quality parameter with respect to the defocus value (FIG. 2). From this curve, it is possible to determine the range in which the patient sees the images sharply enough or the pseudo-accommodation range.

The invention claimed is:

1. A system for characterizing the optical quality and the pseudo-accommodation range of multifocal means used for correcting visual defects, applicable to bifocal, multifocal or progressive intraocular lenses or contact lenses, multifocal ablation or other multifocal configurations, integrating means for projecting an image of a point light source on a retina of a patient through a collimated light beam, and means for directly recording the light reflected, included in a light beam reflected from said retina, in said retina following double passage of the light through ocular means of the patient, comprising a focus corrector device in the illumination path, wherein the system comprises a first focus correction device inserted in the path of the collimated light beam guided towards the retina and a second focus correction device inserted in the light beam reflected from the retina to be guided towards the mentioned recording means, each of said first and second focus correction devices having independent control means for controlling operation of an associated one of the first and second focus correction devices, such that existence and independence of the independent control means for both the first and second focud correction devices allow focusing the point light source on the retina of the patient through any of the focal points of the multifocal means and introducing any defocus in the recording path at the same time.

2. The system according to claim 1, wherein said first and second focus correction devices comprise respective motorized optometers including two lenses and two mirrors with an adjustable relative distance between the two lenses and the two mirrors of each optometer, wherein said motorized optometers form part of a double-pass ophthalmoscopic device.

3. The system according to claim 1, wherein said first and second focus correction devices only comprise two lenses with a variable distance between the two lenses, wherein said two lenses of said first focus correction device and said two lenses of said second focus correction device form part of a double-pass ophthalmoscopic device.

4. The system according to claim 1, wherein at least one of said first and second focus correction devices comprises a lens with a variable power forming part of a double-pass ophthalmoscopic device.

5. The system according to claim 1, further including means for displaying a fixation stimulus to the patient which overlaps the collimated light beam focused on the retina.

6. The system according to any one of the preceding claims, characterized by including means for viewing patient's eye by means of an illumination system and of a system for forming an image of an eye of the patient in a recording means.

7. The system according to claim 1, further comprising optical entrance and exit pupils with a variable diameter, both of said optical entrance and exit pupils being in a plane conjugated with the pupil of patient's eye.

8. A method for characterizing the optical quality and the pseudo-accommodation range of multifocal means used for correcting visual defects by means of analyzing retinal images of bifocal, multifocal or progressive intraocular lenses or contact lenses, multifocal ablation or other multifocal configurations through retinal image analysis, said method comprising projecting the image of a point light source on the retina of a patient through a light beam of an illumination path, and directly recording, from a light beam of a recording path, light reflected in said retina after the double passage of the light through ocular means of the patient, the method further comprising at least one focus correcting step both in the illumination path and in the recording path.

9. The method according to claim 8, further comprising two independent focus correcting steps, the first step is performed on the light beam of the illumination path and the second step is performed on the light beam of said recording path, providing an asymmetrical focus and the examination of the two near vision and far vision foci and of any focus corresponding to intermediate vision.

10. The method according to claim 8, further comprising a step of applying some means for displaying a fixation stimulus to the patient which overlaps the light beam projected on the retina.

\* \* \* \* \*